United States Patent [19]

King

[11] Patent Number: 4,686,225
[45] Date of Patent: Aug. 11, 1987

[54] VINPOCETINE FOR PULMONARY HEMORRHAGE AND EDEMA

[75] Inventor: Gary A. King, Lawrenceville, N.J.

[73] Assignee: American Home Products Corporation (Del.), New York, N.Y.

[21] Appl. No.: 857,202

[22] Filed: Apr. 29, 1986

[51] Int. Cl.$^4$ ............................................. A61K 31/44
[52] U.S. Cl. .................................................... 514/283
[58] Field of Search ......................................... 514/283

[56] References Cited

U.S. PATENT DOCUMENTS 4,035,370  7/1977  Lörincz et al. ...................... 514/929

FOREIGN PATENT DOCUMENTS 0042526  12/1981  European Pat. Off. ............ 514/283
2475549   8/1981  France ................................ 514/283

Primary Examiner—Allen J. Robinson
Attorney, Agent, or Firm—John W. Routh

[57] ABSTRACT

A method is disclosed for inhibiting pulmonary hemorrhage and edema associated with intracranial syndromes such as trauma, tumor, hemorrhage and stroke by administering an effective amount of vinpocetine.

4 Claims, No Drawings ically, a parenteral dose or an oral dose is administered in one to four applications per day. Such doses are considered to be an effective amount when, following their

VINPOCETINE FOR PULMONARY HEMORRHAGE AND EDEMA

BACKGROUND OF THE INVENTION (a) Field of the Invention

This invention relates to a novel therapeutic use of apovincaminic acid ethyl ester. More specifically this invention relates to a method for inhibiting pulmonary hemorrhage and edema associated with intracranial syndromes such as trauma, tumor, hemorrhage and stroke.

(b) Prior Art

The active agent of this invention, apovincaminic acid ethyl ester, is disclosed in U.S. Pat. No. 4,035,370, issued July 12, 1977. This active agent, hereinafter designated by its generic name vinpocetine, previously has been reported to have cerebral vasodilatory activity and to have a desirable influence on the cerebral vascular flow, a desirable influence on the heart functions and to stimulate the metabolism of the cerebral tissues (See U.S. Pat. No. 4,035,370). It has been found unexpectedly that vinpocetine is useful for inhibiting pulmonary hemorrhage and edema associated with intracranial syndromes such as trauma, tumor, hemorrhage and stroke.

This finding, coupled with the fact that vinpocetine is a relatively safe drug, renders the method of this invention particularly useful and advantageous.

SUMMARY OF THE INVENTION

According to this invention a method is provided for inhibiting pulmonary hemorrhage and edema associated with intracranial syndromes such as trauma, tumor, hemorrhage and stroke in a mammal in need of said treatment which comprises administering to the mammal an affective amount of vinpocetine.

DETAILS OF THE INVENTION

According to the present method, vinpocetine is employed as the active agent. Examples of other suitable ester forms of apovincaminic acid are described in U.S. Pat. No. 4,035,370 and include the butyl ester, the allyl ester, the benzyl ester, and the ethyl ester methoiodide forms. The preferred ester form is the ethyl ester, i.e. apovincaminic acid ethyl ester, vinpocetine.

Vinpocetine is administered to humans suffering from intracranial syndromes either orally or parenterally. For many reasons oral administration is preferred.

While vinpocetine can be administered alone, e.g. as a sole component of a filled capsule, it is preferred to formulate the compound in various dosage forms for oral or parenteral administration, e.g. tablets, or sterile solutions. Such formulations are described in U.S. Pat. No. 4,035,370, herein incorporated by reference in its entirety, and are otherwise well known to those skilled in the art.

When utilizing vinpocetine as an agent for inhibiting pulmonary hemorrhage and edema associated with intracranial syndromes, the total dose of active agent can range from 10 to 200 milligrams per kilogram of body weight per day with a preferred dosage range for humans being from 5 to 150 milligrams per day and most preferably 30 to 100 milligrams per day. Generally, a parenteral dose or an oral dose is administered in one to four applications per day. Such doses are considered to be an effective amount when, following their administration, a decrease in pulmonary hemorrhage and edema is experienced by the patient.

The effectiveness of vinpocetine in inhibiting pulmonary hemorrhage and edema has been demonstrated in laboratory animals.

EXAMPLE I

Animals

Male F-344 rats were obtained from Charles River Breeding Labs (Wilmington, MA) and kept four per cage for at least one week prior to treatment, with food and water available ad lib. The rats weighed between 182-230 grams at the start of the experiment.

Drug used

Vinpocetine was dissolved in 0.1N HCl, and pH was adjusted to 2.9 with NaOH. Drug or the appropriate vehicle was injected i.p. in a volume of 3 ml/kg.

Procedure

Surgery was performed on rats in groups of 10-12, beginning at 0700 hours. Anesthesia was induced with 3% halothane in 95% $O_2$, 5% $CO_2$. The carotid arteries were exposed and carefully dissected free of surrounding connective tissue and nerve fibers. Two 3-0 sutures, separated by 2-3 mm, were tied tightly around each artery, and the arteries were severed between the sutures. This surgical procedure in which the carotid arteries were surgically occluded bilaterally will hereinafter be referred to as BCAO. The wound was closed with clips, and the rat was allowed to recover from anesthesia. The operation required approximately ten minutes. Animals were dosed acutely immediately following BCAO. Following surgery, the rats were grouped three or four per cage (37.5 cm×25.4 cm×22.9), and a 60 watt lamp was positoned 20 cm above the top of each cage to provide heat.

Rats which survived surgery were observed for eight hours. If death occurred prior to eight hours, the animal was weighed, and the pleural cavity opened. The lungs were observed, and the presence or absence of hemorrhagic changes was noted. Then the lungs were removed, blotted on absorbent paper, and weighed.

Rats which survived the eight-hour observation period were killed by cervical dislocation, and the lungs were processed as described above. Lung weight was expressed as percent body weight (% L/B) according to the following formula:

$$\frac{100 \times \text{lung weight}}{\text{body weight}} \% \text{ L/B}$$

Other data which were recorded for each rat included latency to the first convulsive episode and latency to death.

Statistic

The number of rats in each group with hemorrhagic and normal appearing lungs was compared by the Fisher Exact test described in "Biostatistics" by A. Goldstein, MacMillan Publishing Co., New York, N.Y. 1986; page 110. The % L/B of operated rats and non-operated controls was compared by means of a Student's t-test ("Biostatistics" cited above). Statistical comparisons between hemorrhagic and nonhemorrhagic rats of variables including % L/B were avoided, because they would be post hoc, and thus invalid.

RESULTS

Occurrence of Pulmonary Hemorrhage in Rats Due to BCAO

The occurrence of pulmonary hemorrhage following BCAO was investigated separtely in drug-free animals. Twenty-four rats were either subjected to BCAO (n=12), or were only anesthetized with halothane (control) group, n=12). All of the control rats and one ischemic rat survived for eight hours. All of the ischemic rats, but none of the control rats, had seizures. In the BCAO group, seven out of 12 rats (58.3%) showed moderate to severe pulmonary hemorrhage; the lungs of the other five ischemic rats were normal in appearance. One control rat had a moderate degree of pulmonary hemorrhage. The two groups differed significantly regarding the occurrence of pulmonary hemorrhage (Fisher's exact test, $p<0.02$).

The mean lung weight of the BCAO group was elevated compared to that of the control group, and this difference was due entirely to the greater number of hemorrhagic rats in the BCAO group. The mean ($\pm$SEM) % L/B for the control group was 0.52 ($\pm$0.03), while the corresponding value for the BCAO group was 0.73 ($\pm$0.08). A student's t-test showed this difference to be statistically significant ($t=2.57$, $p<0.02$, $DF=22$). If the hemorrhagic animals are excluded from the calculations, the mean ($\pm$SEM) % L/B for the control group was 0.48 ($\pm$0.01, $n=11$), while that of the ischemic group was 0.47 ($\pm$0.01, $n=5$).

Effects of Vinpocetine

Vinpocetine at 50 and 100 mg/kg almost completely prevented the occurrence of pulmonary hemorrhage after BCAO (Table 1). The mean value of % L/B for the vinpocetine-treated groups was similar to that of vehicle-treated ischemic rats with normal lungs and less than one-half the value of vehicle-treated rats with pulmonary hemorrhage (Table 1).

Vinpocetine increased the latency to the first convulsion when compared to the vehicle control group (Table 1). This effect was significant at 100 mg/kg but not at 50 mg/kg.

Bilateral carotid artery occlusion (BCAO) in the Fisher rat resulted in pulmonary hemorrhage and edema in a significant number of animals within eight hours post-surgery. If the results from all nondrug-treated rats reported on in the study are pooled, 22 out of 43 rats (67%) developed pulmonary hemorrhage following BCAO. Vinpocetine at 50 and 100 mg/kg, i.p., doses which had been shown to delay the onset of ischemic convulsions, prevented pulmonary hemorrhage and edema. Pulmonary hemorrhage has also been reported by others to occur as a consequence of experimentally-induced cerebral concussion in rats. See, for example, an article by Beckman et al, entitled "Pulmonary damage and head injury" in Proc. Soc. Exp. Biol. Med. 1969; 130:5-9 and an article by Bean et al, entitled "Centrogenic pulmonary pathology in mechanical head injury" in J. Appln Physiol. 1969; 27: 807-812.

In the concussion model of brain trauma, pulmonary hemorrhage is claimed to be a consequence of excessive sympathetic stimulation in the first of the above articles and can be blocked by sympatholytic agents as described in the second article. Vinpocetine, however, does not have sympatholytic effects and therefore many prevent pulmonary hemorrhage following BCAO as a consequence of its anti-ischemic activity.

The results shown in Table 1 indicate that vinpocetine treatment of humans in the acute phase of stroke and soon after head injury may provide additional therapeutic benefits thought the prevention of pulmonary hemorrhage and edema without introducing unwanted sympatholytic effects. Corresponding therapeutic benefits may be provided in humans suffering from brain tumors.

I claim:

1. A method for inhibiting pulmonary hemorrhage and edema associated with a intracranial syndrome in a mammal in need of such treatment which comprises administering to the mammal an effective amount of vinpocetine.

2. The method of claim 1 in which the effective amount of vinpocetine is within the range of from 10 to 200 milligrams per kilogram of body weight.

3. The method of claim 1 in which the effective amount of vinpocetine for human therapy is within the range of from 50 to 150 milligrams per day.

4. The method of claim 1 in which the intracranial syndrome is selected from the group consisting of trauma, tumor, hemorrhage and stroke.

TABLE 1

Effect of Vinpocetine on the Occurrence of Pulmonary Hemorrhage and Edema, and the Latency to Convulsion Following BCAO in Fisher Rats.

| Drug | Dose (mg/kg i.p.) | Nonhemorrhagic | | | Hemorrhagic | | |
|---|---|---|---|---|---|---|---|
| | | n | % L/B[a] x + (SE) | Convulsion Latency (HRS) MEDIAN ($Q_1$, $Q_3$) | n | % L/B[a] x + (SE) | Convulsion Latency (HRS) MEDIAN ($Q_1$, $Q_3$) |
| VINPOCETINE | 0 | 7 | 0.45 + 0.02 | 1.93(1.78,4.07) | 17 | 0.86 = 0.07 | 2.27(1.87,2.53) |
| | 50 | 10 | 0.42 ± 0.01 | 3.06(2.72,3.64) | 1[b] | 0.57 | 2.07 |
| | 100 | 12 | 0.42 ± 0.01 | 3.40(2.49,5.40) | 0[b] | — | — |

[a] % L/B = Lung weight as percent of body weight
[b] Different than vehicle, $p<0.001$